United States Patent [19]

Hasspacher et al.

[11] Patent Number: 4,980,359
[45] Date of Patent: Dec. 25, 1990

[54] ISOQUINOLINE DERIVATIVES AND THEIR USE

[75] Inventors: Klaus Hasspacher, Riehen; Reto Naef, Rheinfelden, both of Switzerland

[73] Assignee: Sandoz Ltd., Basel, Switzerland

[21] Appl. No.: 507,702

[22] Filed: Apr. 10, 1990

Related U.S. Application Data

[63] Continuation of Ser. No. 294,431, Jan. 6, 1989, abandoned.

[30] Foreign Application Priority Data

Jan. 8, 1988 [GB] United Kingdom ............... 8800397

[51] Int. Cl.$^5$ .................... A61K 31/47; G07D 217/16
[52] U.S. Cl. ...................................... 514/307; 546/144
[58] Field of Search ......................... 546/144; 514/307

[56] References Cited

U.S. PATENT DOCUMENTS

| | | | |
|---|---|---|---|
| 3,878,215 | 4/1975 | Houlihan et al. | 546/144 |
| 4,018,927 | 4/1977 | Vorhees | 514/307 |
| 4,547,508 | 10/1985 | Konz et al. | 546/144 |
| 4,785,104 | 11/1988 | Rubloczky et al. | 546/144 |

FOREIGN PATENT DOCUMENTS

| | | |
|---|---|---|
| 251361 | 1/1988 | European Pat. Off. |
| 2811361 | 9/1979 | Fed. Rep. of Germany |
| 3244594 | 6/1984 | Fed. Rep. of Germany |
| 1362765 | 4/1964 | France |
| 645139 | 10/1950 | United Kingdom |

OTHER PUBLICATIONS

Heterocycles, vol. 9, No. 1, pp. 1-6, (1978).
J. Med. Chem., vol. 22, No. 4, pp. 348-352, (1979).
Hasspacher et al., "Chemical Abstracts", vol. 112, 1990, col. 112:76968y.

Primary Examiner—Glennon H. Hollrah
Assistant Examiner—James H. Turnipseed
Attorney, Agent, or Firm—Gerald D. Sharkin; Robert S. Honor; Joseph J. Borovian

[57] ABSTRACT

Compounds of formula I

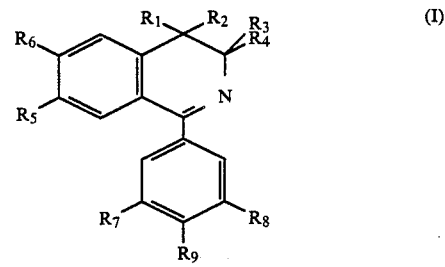

wherein $R_1$ is hydrogen or $C_{1-4}$alkyl; $R_2$ is hydrogen and $R_3$ is hydrogen or $C_{1-4}$alkyl, or $R_2$ and $R_3$ together represent an additional bond as indicated by the dotted line; $R_4$ is hydrogen, $C_{1-4}$alkyl or phenyl; $R_5$ is methoxy or ethoxy; $R_6$ is hydrogen, hydroxy, $C_{1-4}$alkoxy, hydroxy-($C_{2-4}$alkoxy) or ($C_{1-4}$alkoxy)-($C_{2-4}$alkoxy); $R_7$ and $R_8$ are each independently $C_{1-4}$alkoxy or ($C_{1-4}$alkoxy)-($C_{2-4}$alkoxy); and $R_9$ is hydrogen or halogen, in free form or pharmaceutically acceptable salt form, have pharmaceutical utility, in particular as bronchodilators, eosinophil accumulation and/or activation inhibiting agents and in the treatment of prophylactic treatment of obstructive or inflammatory airways diseases.

9 Claims, No Drawings

ISOQUINOLINE DERIVATIVES AND THEIR USE

This is a continuation of application Ser. No. 07/294,431, filed Jan. 6, 1989, now abandoned.

The present invention relates to novel isoquinoline derivatives having pharmaceutical utility, processes for their production, pharmaceutical compositions comprising them and their use as pharmaceuticals.

More particularly the present invention provides compounds of formula I

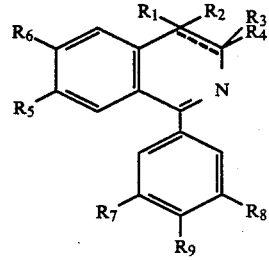

wherein
- $R_1$ is hydrogen or $C_{1-4}$alkyl;
- $R_2$ is hydrogen and
- $R_3$ is hydrogen or $C_{1-4}$alkyl, or
- $R_2$ and $R_3$ together represent an additional bond as indicated by the dotted line;
- $R_4$ is hydrogen, $C_{1-4}$alkyl or phenyl;
- $R_5$ is methoxy or ethyxy;
- $R_6$ is hydrogen, hydroxy, $C_{1-4}$alkoxy, hydroxy-($C_{2-4}$alkoxy) or ($C_{1-4}$alkoxy)-($C_{2-4}$alkoxy);
- $R_7$ and $R_8$ are each independently $C_{1-4}$alkoxy or ($C_{4-4}$alkoxy)-($C_{2-4}$alkoxy); and
- $R_9$ is hydrogen or halogen and their acid addition salts.

In the compounds of formula I, alkyl groups and moieties may be branched or straight chain. Suitably they are straight chain. By halogen is meant fluorine, chlorine, bromine or iodine.

In the compounds of formula I, the following significances are preferred either individually or in any combination or sub-combination:

(1) $R_2$ and $R_3$ together represent an additional bond.
(2) $R_5$ is methoxy.
(3) $R_6$ is other than hydrogen. Preferably $R_6$ is hydroxy, methoxy, ethoxy, β-hydroxy-ethoxy or $C_{1-2}$alkoxy-ethoxy. More preferably $R_6$ is methoxy.
(4) $R_7$ and $R_8$ are identical. Suitably they are each independently ($C_{1-4}$alkoxy)-($C_{2-4}$alkoxy), e.g. ($C_{1-4}$alkoxy)-ethoxy. More suitably they are identical ($C_{1-4}$alkoxy)-($C_{2-4}$alkoxy), e.g. ($C_{1-4}$alkoxy)-ethoxy.

Preferred halogen as $R_9$ is chlorine or bromine, particularly bromine.

In the case of hydroxy-($C_{2-4}$alkoxy) and ($C_{1-4}$alkoxy)-($C_{2-4}$alkoxy) groups as $R_5$, $R_6$, $R_7$ and $R_8$, the hydroxy/($C_{1-4}$alkoxy) moiety is separated from the oxygen atom of the ($C_{2-4}$alkoxy) moiety by at least 2 carbon atoms.

In one group of compounds in accordance with the invention $R_9$ is hydrogen.

Compounds of the formula I exist in both free and acid addition salt form. Suitable pharmaceutically acceptable acid addition salt forms for use in accordance with the present invention as hereinafter described include, for example the hydrochloride, oxalate and fumarate salts.

Compounds of formula I wherein $R_2$ and $R_3$ do not represent an additional bond and wherein [$R_1$ and $R_2$] and/or [$R_3$ and $R_4$] are different exhibit optical isomerism. Similarly compounds of formula I wherein substituents $R_1$ through $R_8$ include one or more asymmetric carbon atoms also exhibit optical isomerism. The present invention is to be understood as embracing both individual isomeric forms as well as mixtures, e.g. racemic and diastereomeric mixtures, thereof unless otherwise specified.

Where compounds of the invention exist in isomeric form as aforesaid, individual isomers may be obtained in conventional manner, e.g. employing optically active starting materials or by separation of initially obtained mixtures, for example using conventional chromatographic techniques.

In a further aspect the present invention also provides a method for the production of compounds of formula I, which method comprises:

(a) subjecting a compound of formula II

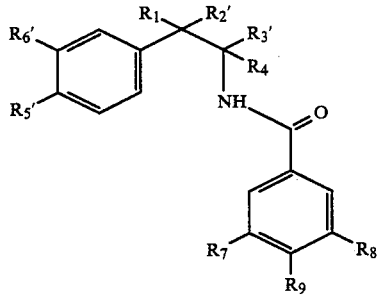

wherein $R_2'$ is hydrogen and $R_3'$ is hydrogen or $C_{1-4}$alkyl, $R_5'$ and $R_6'$ have the meanings given for $R_5$ and $R_6$ in formula I, with the proviso that any hydroxy group present is in protected form, and $R_1$, $R_4$, $R_7$, $R_8$ and $R_9$ have the meanings given for formula I, to dehydrative cyclization and, when required, removing protective groups present in $R_5'$ and $R_6'$ to produce the corresponding compound of formula I wherein $R_2$ is hydrogen and $R_3$ is hydrogen or $C_{1-4}$alkyl; and (b) dehydrogenating a compound of formula I wherein $R_2$ and $R_3$ are each hydrogen, to produce the corresponding compound of formula I wherein $R_2$ and $R_3$ together represent an additional bond;

and recovering the obtained compound of formula I in free or acid addition salt form.

Process step (a) above may be performed in accordance with methods known and practiced in the art, for example by reaction of II with a phosphoroxy-trihalide in the presence of an inert solvent or diluent such as acetonitrile at temperatures of from e.g. 50° C. to reflux. Where end-products are desired in which $R_6$ and/or $R_7$ comprises a hydroxy moiety the hydroxy group(s) in the starting material will be in protected form. Suitable protecting groups include any of these known and commonly employed in the art including $C_{1-4}$alkoxy groups such as methoxy. The deprotection step defined in process step a) thus includes cleavage of the $C_{1-4}$alkoxy moiety in compounds of formula I wherein $R_5$ and/or $R_6$ is $C_{1-4}$alkoxy or ($C_{1-4}$alkoxy)-($C_{2-4}$alkoxy) to obtain the corresponding compounds of formula I wherein $R_5$ and/or $R_6$ is hydroxy or hydroxy-($C_{2-4}$alkoxy). By choice of appropriate protective groupings and reaction conditions compounds of formula I may be obtained in which hydroxy-containing substituents are present as $R_5$ and/or $R_6$.

The starting materials for process step (b) may be obtained in accordance with the procedures of step (a). Dehydrogenation can be effected by any of the means known in the art, for example employing an appropriate catalyst such as Pd/charcoal, carrying out reaction in an inert solvent or diluent under an inert atmosphere at a temperature of from 100° to 250° C.

Starting materials of formula II required for process step a) are known or may be prepared analogously to the known starting materials for example by reaction of a compound of formula III

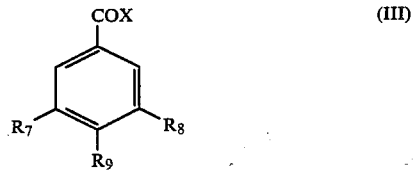

wherein X represents a leaving group or atom, for example halogen atom, such as chlorine, with a compound of formula IV

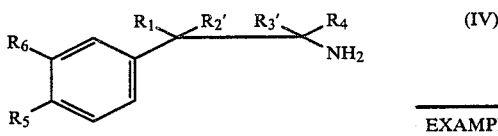

wherein $R_2'$ and $R_3'$ have the meanings given for formula II and $R_5$ and $R_6$ are protected if and as required. The reaction may for example be carried out in an inert medium such as $CH_2Cl_2$ employing a suitable base, e.g. when X=Cl, for example alkali metal hydroxide such as NaOH, at a temperature of from ca. 0° to 50° C.

The following examples are illustrative of the above methods for the preparation of the compounds of formula I.

EXAMPLE 1

Preparation of 3-methyl-6,7-dimethoxy-1-(3,5-dimethoxyethoxyphenyl)-3,4-dihydro-isoquinoline. [Formula I: $R_1$, $R_2$, and $R_3$ each=H; $R_4$=$CH_3$-; $R_5$ and $R_6$ each=$CH_3O$-; $R_7$ and $R_8$ each=$CH_3O$-$CH_2$-$CH_2$-O-;$R_9$=H]

170g N-{3-(3,4-dimethoxy-phenyl)-2-propyl}-3,5-dimethoxyethoxybenzamide (Formula II: $R_1$, $R_2'$ and $R_3'$ each H; $R_4$=$CH_3$-; $R_5'$ and $R_6'$ each=$CH_3O$-; $R_7$ and $R_8$ each=$CH_3O$-$CH_2$-$CH_2$-O-and $R_9$=H) is suspended in 700 ml acetonitrile and 52 ml phosphoroxytrichloride and the reaction mixture heated under reflux for 5 hrs. The solvent is removed under reduced pressure and the residue treated with 300 ml 15% aqueous NaOH for 1 hr. The mixture is extracted with ethyl acetate, the organic layer evaporated and the residue purified chromatographically employing silica gel and ethyl acetate as mobile phase to yield the title compound: m.p. for the oxalate=161° to 162° C.

The following compounds of formula I may be prepared analogously:

EXAMPLE 2

$R_1$, $R_2$ and $R_3$ each=H
$R_4$=phenyl
$R_5$ and $R_6$ each=$CH_3O$-
$R_7$ and $R_8$ each=$CH_3O$-$(CH_2)_2$-O-
$R_9$=hydrogen
m.p. for the oxalate salt=126°-128° C.

| EXAMPLE | $R_1$ | $R_2$ | $R_3$ | $R_4$ | $R_5$ | $R_6$ |
|---|---|---|---|---|---|---|
| 3 | H | H | H | H | $CH_3O$— | $CH_3O$— |
| 4 | H | H | H | H | $C_2H_5O$— | $C_2H_5O$— |
| 5 | $CH_3$ | H | H | H | $CH_3O$— | $CH_3O$— |
| 6 | H | H | $CH_3$— | H | $CH_3O$— | $CH_3O$— |
| 7 | H | H | $C_2H_5$— | H | $CH_3O$— | $CH_3O$— |
| 8 | H | H | $nC_3H_7$— | H | $CH_3O$— | $CH_3O$— |
| 9 | H | H | $CH_3$— | $CH_3$— | $CH_3O$— | $CH_3O$— |
| 10 | H | H | H | H | $CH_3O$— | $CH_3O$—$(CH_2)_2$—O— |
| 11 | H | H | H | $CH_3$ | $CH_3O$— | $CH_3O$— |

| EXAMPLE | $R_7$ | $R_8$ | $R_9$ | m.p. (°C.) |
|---|---|---|---|---|
| 3 | $CH_3O$— | $CH_3O$— | H | 84–85 |
| 4 | $CH_3O$— | $CH_3O$— | H | 85–86 |
| 5 | $CH_3O$— | $CH_3O$— | H | 183–184 (1) |
| 6 | $CH_3O$— | $CH_3O$— | H | 119–121 |
| 7 | $CH_3O$— | $CH_3O$— | H | 176–178 |
| 8 | $CH_3O$— | $CH_3O$— | H | 104–105 |
| 9 | $CH_3O$— | $CH_3O$— | H | 199–201 (1) |
| 10 | $CH_3O$— | $CH_3O$— | H | 136–138 (2) |
| 11 | $CH_3O$—$(CH_2)_2$—O— | $CH_3O$—$(CH_2)_2$—O— | Br | 140–142 |

(1) as the fumarate salt
(2) as the oxalate salt

EXAMPLE 12

Preparation of 3-methyl-6,7-dimethoxy-1-(3,5-dimethoxyethoxyphenyl)-isoquinoline. [Formula I: $R_1$=H,$R_2$ and $R_3$ together=an additional bond; $R_4$=$CH_3$-;$R_5$ and $R_6$ each=$CH_3O$-; $R_7$ and $R_8$ each=$CH_3O$-$CH_2$-$CH_2$-O-;$R_9$=H]

20 g of the product of example 1 and 4g 10% palladium on charcoal in 200 ml decaline are heated to 200° C., for 5 hrs. with argon gassing. 300 ml ethyl acetate are added following cooling, the catalyst is filtered off and the solvent evaporated under reduced pressure. The residue is purified chromatographically employing silica gel and ethyl acetate to yield the title compound: m.p. for the oxalate=165° to 167° C.

The following compounds of formula Ia

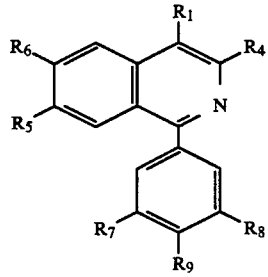

wherein $R_1$ and $R_4$ to $R_9$ are as defined below may be prepared analogously.

| EXAMPLE | $R_1$ | $R_4$ | $R_5$ | $R_6$ | $R_7$ | $R_8$ | $R_9$ | m.p. (°C.) |
|---|---|---|---|---|---|---|---|---|
| 13 | H | H | $CH_3O-$ | $CH_3O-$ | $CH_3O-$ | $CH_3O-$ | H | 140–143 |
| 14 | H | $CH_3-$ | $CH_3O-$ | $CH_3O-$ | $CH_3O-$ | $CH_3O-$ | H | 213–215 (3) |
| 15 | $CH_3$ | H | $CH_3O-$ | $CH_3O-$ | $CH_3O-$ | $CH_3O-$ | H | 197–199 (1) |
| 16 | $CH_3-$ | $CH_3-$ | $CH_3O-$ | $CH_3O-$ | $CH_3O-$ | $CH_3O-$ | H | 203–205 (1) |
| 17 | H | $C_2H_5-$ | $CH_3O-$ | $CH_3O-$ | $CH_3O-$ | $CH_3O-$ | H | 210–212 (3) |
| 18 | H | $nC_3H_7-$ | $CH_3O-$ | $CH_3O-$ | $CH_3O-$ | $CH_3O-$ | H | 196–197 (3) |
| 19 | H | $CH_3-$ | $CH_3O-$ | $CH_3O-(CH_2)_2-O-$ | $CH_3O-(CH_2)_2-O-$ | $CH_3O-(CH_2)_2-O-$ | H | 111–114 (4) |
| 20 | H | $CH_3$ | $CH_3O-$ | $CH_3O-$ | $CH_3O-(CH_2)_2-O-$ | $CH_3O-(CH_2)_2-O-$ | Br | 147–149 |

(1)fumarate salt
(3)hydrochloride salt
(4)hydrobromide salt

EXAMPLE 21

Preparation of 6-hydroxy-7-methoxy-1-(3,5-dimethoxyphenyl)-3,4-dihydroisoquinoline. [Formula I: $R_1$, $R_2$, $R_3$ and $R_4$=H; $R_5$=$CH_3O-$; $R_6$=HO; $R_7$ and $R_8$=$CH_3O-$;$R_9$=H]-Deprotection step.

3.2 g of the product of example 3, 15 ml 15% aqueous HBr and 6 ml $H_2O$ are heated under influx for 18 hrs. The reaction mixture is extracted with ethyl acetate, the organic phase is evaporated off and the residue purified chromatographically employing silica gel and ethyl acetate as mobile phase to yield the title compound: m.p.=109°–111° C.

EXAMPLE 22

The compound of formula Ia above wherein $R_1$=H; $R_4$=$CH_3$-; $R_5$=$CH_3O-$; $R_6$=HO-$(CH_2)_2$-O-; $R_7$ and $R_8$ each=$CH_3O-(CH_2)_2$-O-; and $R_9$=H may be prepared analogously to example 21 starting from the product of example 18: m.p. 179°–180° C.

Compounds of formula I and their pharmaceutically acceptable acid addition salts exhibit pharmacological activity and are therefore indicated for use as pharmaceutical agents, e.g. for therapy. In particular they are useful as bronchodilator and asthma-prophylactic agents as well as agents for the inhibition of eosinophil accumulation, e.g., for the treatment of inflammatory airways disease, especially asthma, as well as for the treatment of other diseases and conditions characterized by, or having an aetiology involving, morbid eosinophil accumulation. These properties may be demonstrated in standard pharmaceutical tests in vivo and in vitro, for example as follows:

EXAMPLE A: BRONCHODILATOR ACTIVITY

1. Bronchospasmolytic activity in vitro

The trachea is excised from freshly sacrificed guinea-pigs (Dunkin-Hatley (350–500 g) and transected in the transverse plane to give rings of tissue of ca. 3–5 mm deep. Individual rings are mounted vertically on stainless steel supports, one of which is fixed at the base of an organ bath, the other being attached to an isometric transducer. The rings are bathed in Krebs solution (composition nM: $NaHCO_3$ 25, NaCl 113, KCl 4.7, $MgSO_4.7H_2$) 1.2, KHhd $2PO_4$ 1.2, $CaCl_2$ 2.5, Glucose 11.7) at 37° C. and gassed with $O_2/CO_2$ (95:5, v/v). Rings prepared in this manner, preloaded with 1 g, generate spontaneous tone and, after a period of equilibration (45–60 min.), relax consistently on addition of spasmolytic drugs. Tension can be enhanced by addition of carbachol ($10^{-6}M$) or histamine ($10^{-4}M$). To assertain spasmolytic activity, test substances are dissolved in physiological saline and added in increasing quantities to the organ bath at 10 min. intervals to provide a cumulative concentration-effect curve.

In the above test model compounds of formula I and their pharmaceutically acceptable acid addition salts produce concentrationrelated relaxation of guinea-pig tracheal ring preparations irrespective of the contractile agency at concentrations of from about $10^{-7}$ to about $10^{-5}$ M.

2. Bronchodilator activity in vivo

Guinea pigs (Dunkin-Hartley, ♂, 400–600 g) are anesthetized with phenobarbital (100-mg/kg i.p.) and pentobarbital (30 mg/kg i.p.) and paralyzed with gallamine (10 mg/kg i.m.). Animals are ventilated via a tracheal cannula (10 ml/kg, 1Hz.). Blood pressure and heart rate are recorded at the carotid artery. Ventilation is monitored by a Fleisch flow transducer in lien with the inspiratory circuit. When making measurements of flow, coincident pressure changes in the thorax are monitored directly via an intrathoracic trochar, permitting display of differential pressure relative to the trachea. From this information resistance and compliance are calculated at each inspiration.

Continuous intravenous infusion of bombesin (50–100 ng/kg/min) induces sustained bronchospasm. Capacity of test-substance to reverse response when administered intra-duodenally via a 12 gauge metal needle fixed by a purse string ligature into the peripheral end of the transected duodenum serves as a measure of efficacy in reversing established bronchospasm.

The bronchodilator response is taken as the percentage reduction of the maximal response to bombesin, measured at regular intervals, up to 64 mins..

In the above test model, compounds of formula I and their pharmaceutically acceptable acid addition salts are found to effect dose related abrogation of bronchospasm at doses of from about 0.1 to about 20.0 mg/kg int. duod..

EXAMPLE B: SUPPRESSION OF AIRWAYS HYPERREACTIVITY
PAF-TREATED ANIMALS

Guinea-pigs are anesthetized and prepared for recording of lung function as described under example A.2. above. Intravenous injection of low dose bombesin (240 ng/kg) establishes airways sensitivity to spasmogens. Following infusion of PAF (platelet activating factor) over 1 hr. (total dose=600 ng/kg), repeated injection of low dose bombesin reveals development of airways hyperreactivity, which can conveniently be expressed as the paired difference between the response amplitude before and after PAF.

On administration of compounds of formula I and their pharmaceutically acceptable acid addition salts by infusion during PAF exposure at dosages of from about 0.1 to about 100 mg/kg, suppression of airways hyperreactivity induction is observed.

EXAMPLE C: INHIBITION OF EOSINOPHIL ACCUMULATION

Guinea-pigs (Dunkin-Hartley 400-600 g) are injected intraperitoneally with 10 μg/kg of PAF, a procedure which produces lung eosinophilia.

Animals are sacrificed with pentobarbital (100 mg/kg i.p.) 24 hours later. The trachea is exposed and cannulated and the airway lumen washed by introduction and aspiration of 10 ml aliquots (x6) of buffered modified Tyrode solution (composition mM: $NaHCO_3$ 11.9, NaCl 136.9, KCl 2.7, $Na_2HPO_4$, glucose 5.6, EDTA 19.8; protein % w/v=gelatin 0.1, BSA 0.5; pH to 7.4 by addition of 2N NaOH). Total fluid recovery generally exceeds 80%.

Cell suspensions are concentrated by low speed centrifugation (200 g for 10 mins.) and the resulting cell pellet is resuspended in 1 ml modified Tyrode solution. Total cell counts are effected in a haemocytometer by diluting 10 μl cell suspension in 90 μl Turks fluid. Differential cell counts are made from smears fixed in 100% methanol and stained with Leishman stain. At least 500 cells smear are counted at 1000 fold magnification to differentiate cell types.

Test compound is administered over 7 days at varying concentration in 1 mg/kg s.c. amounts with exposure to PAF occurring 5 days after commencement of test compound administration.

On administration of compounds of formula I and their pharmaceutically acceptable acid addition salts in the above test model at dosage rates of from about 0.1 to about 200 mg/kg/day s.c. in advance of PAF, decrease in lung eosinophil accumulation is observed as compared with untreated controls.

Having regard to their bronchospasmolytic activity as evidenced in test methods as described in example A above, compounds of formula I and their pharmaceutically acceptable acid addition salts are useful as bronchodilators, e.g. for the treatment, e.g. symptomatic treatment of obstructive or inflammatory airways disease, for example asthma, pneumoconiosis or bronchitis. Having regard to their activity a) in inhibiting acute response in hypersensitive subjects following allergen or other challenge eliciting hypersensitivity reaction (e.g. following induction of hyperreactivity and airways obstruction via PAF challenge), (b) in suppressing development of airways hyperreactivity subsequent to challenge as under (a), and (c) in diminishing basal, or on-going, airways hyperreactivity, as evidenced in test methods as described in example B above, compounds of formula I and their pharmaceutically acceptable acid addition salts are useful in the prophylactic treatment of obstructive or inflammatory airways disease, for example the prophylactic treatment of pneumoconiosis and, in particular, asthma.

[For further discussion of the relevance of (a), (b) and (c) above and their relationship to prophylactic utility in treating inflammatory airways disease, see e.g.: Altounyan, Clin. Allergy (supp.) 10, 481–489 (1980); Morley et al., Lancet ii, 1142–1144 (1984); Mazoni et al., J. Physiol., 365, 107 P (1985); Traietti et al., Respiration, 46, 62–63 (1984); Taytard et al., Am. Rev. Respiratory Disease, 134, 983–985 (1986); Szezeklik et al., Thrombosis and Hematosis, 56, 283–287 (1986); Basran et al., Clin. Allergy, 14, 75–79 (1984); Karlsson et al., Brit. J. Clin. Pharmacol. 27, 371–374 (1985); and Mazzoni et al., Brit. J. Pharmacol., 86, 571 P (1985)].

Thus compounds of formula I and their pharmaceutically acceptable acid addition salts may, by continued administration, be used to provide advance protection against recurrence of bronchoconstrictor attack consequential to obstructive or inflammatory airways disease, e.g. asthma, or for the control, restriction or reversal of basal status of such disease, e.g. for the control, restriction or reversal of basal causes of asthma and asthma attack. The words "treatment" and "treating" as used throughout the present specification and claims are accordingly to be understood as including prophylactic as well as symptomatic modes, unless otherwise specified.

In accordance with the foregoing the present invention accordingly also provides:

1. A method for the treatment of obstructive or inflammatory airways disease in a subject in need thereof, which method comprises administering to said subject an effective amount of a compound of formula I or a pharmaceutically acceptable acid addition salt thereof for example:

Ia. A method of effecting bronchodilation in a subject in need thereof (for example a subject exhibiting obstructive or inflammatory airways disease or airways obstruction, including chronic or acute obstruction, for example as occurring in the symptomatology of diseases, disorder or conditions as herein set forth), which method comprises administering to said subject a bronchodilatorily effective amount of a compound of formula I or a pharmaceutically acceptable acid addition salt thereof; or Ib. A method for the prophylactic treatment of obstructive or, more particularly, inflammatory airways disease (e.g. for advance protective treatment against acute airways obstruction, for example bronchospasm, e.g. as occurring in the symptomatology of diseases, disorders or conditions as herein set forth) in a subject in need thereof, which method comprises administering to said subject a prophylactically effective amount of a compound of formula I or a pharmaceutically acceptable acid addition salt thereof.

In the alternative the present invention provides:

II. A compound of formula I or pharmaceutically acceptable acid addition salt thereof for use as a pharmaceutical, for example for use in the treatment of obstructive or inflammatory airways disease, e.g. for use in a method as defined under I, Ia or Ib above.

The method of the present invention as defined under I to Ib above is, in particular, applicable to the treatment of asthma of whatever type or genesis. It is applicable to both intrinsic and, especially, extrinsic asthma. It is especially applicable to the treatment of allergic asthma, whether atopic, (i.e. IgE-mediated) or non-atopic, as well as e.g. bronchitic asthma, thymic asthma, excercise induced asthma, occupational asthma, asthma induced following bacterial infection and other non-allergic asthmas. Treatment of asthma is also to be understood as embracing treatment of subjects, e.g. of less that 4 or 5 years of age, exhibiting wheezing symptoms, in particular at night, and diagnosed or diagnozable as "wheezy infants", an established patient category of major medical concern and now more correctly identified as incipient or early-phase asthmatics. (For convenience of definition this particular asthmatic condition is referred to hereinafter as "wheezy-infant syndrome").

In a series of particular embodiments the present invention thus provides for treatment of asthma, in particular allergic asthma (for example allergic atopic asthma), exercise induced asthma and wheezy-infant syndrome, including symptomatic treatment of asthma (e.g. bronchodilator treatment of asthma exacerbation or attack) as well as prophylactic treatment of asthma (e.g. prophylactic treatment of asthma exacerbation or attack), comprising use of or administration of a compound of formula I or a pharmaceutically acceptable acid addition salt thereof.

The method of the present invention as defined under I to Ib above is also applicable to the treatment of pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and, in particular, byssinosis.

In a further series of particular embodiments the present invention thus also provides for the treatment of pneumoconiosis, in particular byssinosis, including symptomatic treatment of airways obstruction (e.g. bronchodilator treatment of acute or chronic airways obstruction, e.g. dyspnea or bronchospasm) attributable thereto, as well as prophylactic treatment of airways obstruction (e.g. advance protective treatment of acute airways obstruction, e.g. bronchospasm) attributable thereto, comprising use or administration of a compound of formula I or a pharmaceutically acceptable acid addition salt thereof.

The method of the present invention as defined under I or, especially, Ia above, is also applicable to the treatment of bronchitis or, more especially, the treatment of chronic or acute airways obstruction, for example, dyspnea, associated therewith. In this respect the present invention is applicable to the treatment of bronchitis of whatever type or genesis, including, for example, acute bronchitis, arachidic bronchitis, catarrhal bronchitis, chronic bronchitis, croupous bronchitis, phthinoid bronchitis and so forth.

In a further series of particular embodiments the present invention accordingly provides for the treatment of bronchitis or, more especially, the symptomatic treatment of airways obstructIon (e.g. bronchodilator treatment of acute or chronic airways obstruction, e.g. dyspnea) attributable thereto, comprising use or administration of a compound of formula I or a pharmaceutically acceptable acid addition salt thereof.

Having regard to activity of the compounds formula I and their pharmaceutically acceptable acid addition salts in suppressing eosinophil accumulation as may be demonstrated in test models such as described in example C above the present invention also provides:

III. A method for the suppression of eosinophil accumulation and/or activation, e.g. for the treatment of disease characterized by or having an etiology comprising morbid eosinophil accumulation and/or activation, in a subject in need of such treatment which method comprises administering to said subject an effective amount of a compound of formula I or a pharmaceutically acceptable acid addition salt thereof;

or, in the alternative:

IV. A compound of formula I or a pharmaceutically acceptable acid addition salt thereof for use in a method as defined under III above.

Diseases as defined under III above include, in particular, hypereosinophilia and the eosinophil related disorders.

Hypereosinophilia is a distinct condition or status of varied etiology characterized by chronic, morbid eosinophil presence in the body tissues generally. The eosinophil-related disorders comprise a distinct and extensively documented indication group, commonly occurring concomitant to another, primary disease or condition. [For more detailed discussion see e.g.: Schatz et al., Medical Clinics of North America, 65, (5), 1055–1071 (1981) and Ottesen et al., "Allergy, Principles and Practice", Eds. E. Middleton, C. Reed and S. Ellis, 584–632, (1987)]. The group includes eosinophil-related disorders of the airways (involving morbid eosinophilic infiltration of pulmonary tissues) as well as of other organs and tissues including, for example, the skin, eye, nasal passages and the gastro-intestinal and urinary tracts.

Eosinophil-related disorders to which the present invention is applicable include those concomitant to atopy or atopic reactions in general (e.g. atopic conditions such as rhinitis, conjunctivitis etc... as set forth below) as well as non-atopic eosinophil-related disorders.

Disorders of the airways to which the present invention is applicable include hypereosinophilia as well as, for example, eosinophil-related disorders of the airways consequential or concomitant to Lüoffler's syndrome, eosinophilic pneumonia, parasitic (in particular metazoan) infestation (including tropical eosinophilia), bronchopulmonary aspergillosis, polyarteritis nodosa (including Churg-Strauss syndrome) as well as eosinophil or, related disorders affecting the airways occasioned by drugreaction.

Other eosinophil-related disorders to which the present invention is applicable include eosinophilia consequential or concomitant to eosinophilic gastroenteritis, Heiner's syndrome, atopic dermatitis, urticaria or angioderma (allergic, recurrent or prolonged), ichthyosis, exfoliative dermatitis or pityriasis rubra, urticaria pigmentosa or mastocytoma, toxic epidermal necrolysis (drug related), dermatitis herpetiformis, allergic rhinitis, hyperplastic sinusitis, interstitial nephritis (drug related), interstitial cystitis, choleostatic hepatotoxicity (drug related), allergic conjunctivitis, vernal conjunctivitis, eosinophilic fasciitis, hypersensitivity angiitis, serous myocarditis or endomyocardial iibrosis, Wiscott- Aldrich syndrome, selective IgA deficiency with atopy, eosinophilic leukemia and eosinophilic granuloma.

As will be appreciated, the present invention is directed primarily to the treatment of hypereosinophilia or eosinophilrelated disorders as such. Where, however, eosinophil-related disorders are concomitant to atopy, for example to any of the atopic diseases or conditions specifically recited above including atopic or allergic forms of dermatitis, urticaria, angioderma, rhinitis, conjunctivitis and gastro-intestinal allergies, the present invention may equally be applicable to the treatment of eosinophil-related disorders as an Integral or basal component thereof. The present invention thus also provides means for the treatment (e.g. symptomatic or prophylactic treatment) of atopy, including each of the said recited atopic diseases or conditions, as such. In treating eosinophil-related disorders concomitant to non-atopic diseases or conditions on the other hand, the compound and salts of the invention will more commonly be administered together with other medication for treatment of the disease or condition with which eosinophilia is associated. Thus in the treatment of eosinophilia consequential to parasitic infection, use will generally be in conjunction with other, anti-parasitic drug therapy.

Where compounds of formula I and their pharmaceutically acceptable acid addition salts are employed in accordance with the method of the invention for the treatment of eosinophilrelated disorders of the airways, e.g. for the treatment of hypereosinophilia as it affects the lungs or for the treatment of pulmonary eosinophilia associated with eosinophilic pneumonia, and the disorder is accompanied by symptoms of airways obstruction, they may be employed either as symptomatic or prophylactic therapy, e.g. either to alleviate or abort, or to provide advance protection against recurrence of, obstruction. More commonly however they will be employed symptomatically, e.g. as a means for the treatment of hypereosinophilia or eosinophilrelated disorders, i.e. in accordance with methods defined under III above.

In a further series of particular embodiments the present invention thus also provides:

(i) for the treatment of hypereosinophilia and of eosinophilrelated disorders, including treatment in accordance with the methods defined under III above, including, in the case of eosinophil-related disorders of the airways associated with airways obstruction, symptomatic treatment of airways obstruction (e.g. bronchodilator treatment of acute or chronic airways obstruction, e.g. dyspnea or bronchospasm) and prophylactic treatment of airways obstruction (e.g. advance protective treatment of acute airways obstruction, e.g. bronchospasm) attributable thereto, comprising use or administration of a compound of formula I or a pharmaceutically acceptable acid addition salt thereof; as well as (ii) for the treatment of atopy, for example for the treatment of any of the atopic diseases or conditions causal to or associated with eosinophil-related disorder as hereinbefore set forth, comprising use or administration of a compound of formula I or a pharmaceutically acceptable acid addition salt thereof.

Dosages employed in practicing the various methods of the present invention will of course vary depending on the particular condition to be treated, the particular compound employed, the mode of administration and the therapy desired. In general however, for the above mentioned uses, in particular for the symptomatic and/or prophylactic treatment of obstructive or inflammatory airways disease, for example, asthma, satisfactory results are achieved at dosages of from about 0.1 to about 200, e.g. from about 0.1 to about 10.0 mg/kg/day, e.g. administered i.v. or intraperitoneally. For larger mammals, for example humans, an indicated daily dosage for oral administration, in particular for the symptomatic and/or prophylactic treatment of obstructive or inflammatory airways disease, for example, asthma, will be in the range of from about 50 to about 500 mg per day, in particular from about 100–300 mg per day, conveniently administered once or in divided doses 2 to 4x/day or in sustained release form. Unit dosage forms for oral administration thus suitably comprise from about 12 to about 500, in particular from about 25 to about 150 or 300 mg of compound of formula I or of a pharmaceutically acceptable acid addition salt thereof, together with a pharmaceutically acceptable diluent or carrier therefor.

The compounds of formula I may be administered in free base form or in pharmaceutically acceptable acid addition salt form. Such salts may be prepared in conventional manner and exhibit the same order of activity as the free bases.

The compounds of the invention and their pharmaceutically acceptable acid addition salts may be administered by any conventional route for use in the recited indications, in particular nasally, enterally, preferably orally, e.g. in the form of tablets or capsules, or parenterally, e.g. in the form of injectable solutions or suspensions.

In accordance with the foregoing the present invention also provides: a pharmaceutical composition comprising a compound of formula I as hereinbefore defined or a pharmaceutically acceptable acid addition salt thereof, together with a pharmaceutically acceptable diluent carrier therefor, e.g. for use in any method as defined above. Such compositions may be manufactured in conventional manner.

As already indicated, dosages required in practicing the method of the present invention will inter al. depend on the particular compound of formula I or acid addition salt thereof employed and its relative potency of action. The preferred compound of formula I for use in accordance with the present invention is the product of example 12. Obtained results for this compound in the methods of EXAMPLES A, B and C hereinbefore described in comparison with the known anti-asthmatic standard theophylline are shown in the following table.

| METHOD OF EXAMPLE | COMPOUND EXAMPLE 12 | THEOPHYLLINE | UNIT |
|---|---|---|---|
| A.1.:IC$_{50}$ = | $3 \times 10^{-7}$ | $7.7 \times 10^{-5}$ | Molar |
| A.2.:ED$_{50}$ = | ~2.0 | 11.0 | mg/kg, intra. duodenally |
| B:ED$_{50}$ = | <1.0 | 5.0 | mg/kg, i.v. |

-continued

| METHOD OF EXAMPLE | COMPOUND EXAMPLE 12 | THEOPHYLLINE | UNIT |
|---|---|---|---|
| C:ED$_{50}$ = | <2.0 | 5.0 | mg/kg/day s.c. |

Indicated daily dosages of the compound of example 12, or any pharmaceutically acceptable acid addition salt thereof, employed in accordance with the invention may accordingly be of the order of from about 5 to 100 mg p.o. to larger mammals, for example humans.

What is claimed is:

1. A compound of formula I

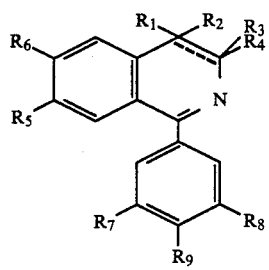

wherein
$R_1$ is hydrogen or $C_{1-4}$alkyl;
$R_2$ is hydrogen and
$R_3$ is hydrogen or $C_{1-4}$alkyl, or
$R_2$ and $R_3$ together represent an additional bond as indicated by the dotted line;
$R_4$ is hydrogen, $C_{1-4}$alkyl or phenyl;
$R_5$ is methoxy or ethoxy;
$R_6$ is hydrogen, hydroxy, $C_{1-4}$alkoxy, hydroxy-($C_{2-4}$ alkoxy) or ($C_{1-4}$alkoxy)-($C_{2-4}$alkoxy);
$R_7$ and $R_8$ are each independently $C_{1-4}$alkoxy or ($C_{1-4}$alkoxy)-($C_{2-4}$alkoxy); and
$R_9$ is hydrogen or halogen,
or an acid addition salt thereof.

2. A compound of formula I according to claim 1, wherein $R_1$ to $R_8$ are as defined in claim 1 and $R_9$ is hydrogen, or an acid addition salt thereof.

3. A compound according to claim 1, wherein $R_2$ and $R_3$ together represent an additional bond, or an acid addition salt thereof.

4. A compound according to claim 1, wherein $R_5$ is methoxy, $R_6$ is other than hydrogen and $R_7$ and $R_8$ are each independently ($C_{1-4}$alkoxy)-($C_{2-4}$alkoxy), or an acid addition salt thereof.

5. A compound according to claim 1, which is selected from the group consisting of
3-methyl-6,7-dimethoxy-1-(3,5-dimethoxyethoxy-phenyl)-3,4-dihydro-isoquinoline,
3-phenyl-6,7-dimethoxy-1-(3,5-dimethoxyethoxy-phenyl)-3,4-dihydro-isoquinoline,
6,7-dimethoxy-1-(3,5-dimethoxy-phenyl)-3,4-dihydroisoquinoline,
6,7-diethoxy-1-(3,5-dimethoxy-phenyl)-3,4-dihydroisoquinoline,
4-methyl-6,7-dimethoxy-1-(3,5-dimethoxy-phenyl)-3,4-dihydroisoquinoline,
3-methyl-6,7-dimethoxy-1-(3,5-dimethoxy-phenyl)-3,4-dihydro-isoquinoline,
3-ethyl-6,7-dimethoxy-1-(3,5-dimethoxy-phenyl)-3,4-dihydroisoquinoline,
3-n-propyl-6,7-dimethoxy-1-(3,5-dimethoxy-phenyl)-3,4-dihydro-isoquinoline,
3,3-dimethyl-6,7-dimethoxy-1-(3,5-dimethoxy-phenyl)-3,4-dihydro-isoquinoline,
7-methoxy-6-methoxy-ethoxy-1-(3,5-dimethoxy-phenyl)-3,4-dihydro-isoquinoline,
6-hydroxy-7-methoxy-1-(3,5-dimethoxyphenyl)-3,4-dihydroisoquinoline,
6,7-dimethoxy-1-(3,5-dimethoxy-phenyl)-isoquinoline,
3-methyl-6,7-dimethoxy-1-(3,5-dimethoxy-phenyl)isoquinoline,
4-methyl-6,7-dimethoxy-1-(3,5-dimethoxy-phenyl)isoquinoline,
1,4-dimethyl-6,7-dimethoxy-1-(3,5-dimethoxy-phenyl)-isoquinoline,
3-ethyl-6,7-dimethoxy-1-(3,5-dimethoxy-phenyl)-isoquinoline,
3-n-propyl-6,7-dimethoxy-1-(3,5-dimethoxy-phenyl)isoquinoline,
3-methyl-6-methoxy-ethoxy-7-methoxy-1-[3,5-di(methoxy-ethoxy)-phenyl]-isoquinoline,
3-methyl-6-β-hydroxy-ethoxy-7-methoxy-1-[3,5-di(methoxyethoxy)-phenyl]-isoquinoline,
and acid addition salts thereof.

6. A compound according to claim 1, which is 3-methyl-6,7-dimethoxy-1-(3,5-dimethoxyethoxyphenyl)-isoquinoline, or an acid addition salt thereof.

7. A compound according to claim 1, which is selected from the group consisting of 3-methyl-6,7-dimethoxy-1-(3,5-dimethoxyethoxy-4-bromo-phenyl)-3,4-dihydro-isoquinoline and 3-methyl-6,7-dimethoxy-1-[3,5-di(methoxy-ethoxy)-4-bromophenyl]-isoquinoline, and acid addition salts thereof.

8. A pharmaceutical composition useful in effecting bronchodilation, suppressing eosinophil accumulation or activation, or in treating obstructive or inflammatory airways disease comprising a pharmaceutically acceptable carrier or diluent and a therapeutically effective amount of a compound of claim 1, or a pharmaceutically acceptable acid addition salt thereof.

9. A method of effecting bronchodilation, suppressing eosinophil accumulation or activation, or treating obstructive or inflammatory airways disease comprising administering to a subject in need of such treatment a therapeutically effective amount of a compound of claim 1, or a pharmaceutically acceptable acid addition salt thereof.

* * * * *